(12) United States Patent
Sullivan et al.

(10) Patent No.: US 12,023,510 B2
(45) Date of Patent: *Jul. 2, 2024

(54) WEARABLE CARDIOVERTER DEFIBRILLATOR (WCD) SYSTEM REACTING TO HIGH-FREQUENCY ECG NOISE

(71) Applicant: West Affum Holdings DAC, Dublin (IE)

(72) Inventors: Joseph Leo Sullivan, Kirkland, WA (US); Jaeho Kim, Redmond, WA (US)

(73) Assignee: West Affum Holdings DAC, Dublin (IE)

( * ) Notice: Subject to any disclaimer, the term of this patent is extended or adjusted under 35 U.S.C. 154(b) by 327 days.

This patent is subject to a terminal disclaimer.

(21) Appl. No.: 17/394,305

(22) Filed: Aug. 4, 2021

(65) Prior Publication Data

US 2021/0361956 A1    Nov. 25, 2021

Related U.S. Application Data

(63) Continuation of application No. 16/037,990, filed on Jul. 17, 2018, now Pat. No. 11,103,717.
(Continued)

(51) Int. Cl.
*A61N 1/39* (2006.01)
*A61N 1/04* (2006.01)
(Continued)

(52) U.S. Cl.
CPC ......... *A61N 1/3904* (2017.08); *A61N 1/0484* (2013.01); *A61N 1/3975* (2013.01);
(Continued)

(58) Field of Classification Search
CPC .. A61N 1/3904; A61N 1/0484; A61N 1/3975; A61N 1/3987; A61N 1/3993; A61B 5/352; A61B 5/7203
(Continued)

(56) References Cited

U.S. PATENT DOCUMENTS 3,724,355 A   4/1973   Busch et al.
3,724,455 A   4/1973   Unger
(Continued)

FOREIGN PATENT DOCUMENTS

WO      9839061 A2    9/1998

OTHER PUBLICATIONS

EPO Search Report dated Dec. 19, 2018 on EP Application No. 1816221.0-1224.
(Continued)

*Primary Examiner* — Erin M Piateski
(74) *Attorney, Agent, or Firm* — Spectrum IP Law Group LLC

(57) ABSTRACT

In embodiments a wearable cardioverter defibrillator (WCD) system is worn by an ambulatory patient. The WCD system analyzes an ECG signal of the patient, to determine whether or not the patient should be given an electric shock to restart their heart. If the WCD system determines that such a shock should be given, then it also determines whether or not a High Frequency (H-F) noise criterion is met by the ECG signal. If that H-F noise criterion is not met, the patient can be shocked. If, however, that H-F noise criterion is met, then the WCD system can confirm before shocking, by sensing another portion of the ECG signal, analyzing again, and so on. Thanks to the confirmation before shocking, the possibility is diminished that the ECG signal will indicate that a shock is needed falsely, due to H-F noise. This can further reduce false patient alarms, and so on.

16 Claims, 10 Drawing Sheets

Related U.S. Application Data

(60) Provisional application No. 62/538,159, filed on Jul. 28, 2017.

(51) Int. Cl.
  *A61B 5/00* (2006.01)
  *A61B 5/352* (2021.01)

(52) U.S. Cl.
  CPC .......... *A61N 1/3987* (2013.01); *A61N 1/3993* (2013.01); *A61B 5/352* (2021.01); *A61B 5/7203* (2013.01)

(58) Field of Classification Search
  USPC ................................................................ 607/7
  See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,381,803 A * | 1/1995 | Herleikson .......... A61B 5/7207 |
| | | 600/521 |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,709,215 A | 1/1998 | Perttu et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,533,165 B1 | 1/2017 | Gunderson |
| 9,592,403 B2 | 3/2017 | Sullivan |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2005/0131476 A1 | 6/2005 | Kim et al. |
| 2008/0306560 A1* | 12/2008 | Macho .................. A61N 1/046 |
| | | 607/5 |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0150008 A1 | 1/2012 | Lanar et al. |
| 2012/0059270 A1* | 3/2012 | Grunwald ............. A61B 5/352 |
| | | 600/509 |
| 2012/0112903 A1 | 5/2012 | Kaib et al. |
| 2012/0144551 A1 | 6/2012 | Guldalian |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0000349 A1* | 1/2016 | Sullivan ............... A61B 5/7221 |
| | | 600/509 |
| 2016/0004831 A1 | 1/2016 | Carlson et al. |
| 2016/0067514 A1 | 3/2016 | Sullivan |
| 2016/0074667 A1 | 3/2016 | Sullivan et al. |
| 2016/0082277 A1 | 3/2016 | Foshee, Jr. et al. |
| 2016/0235320 A1* | 8/2016 | Sarkar .................. A61N 1/3624 |
| 2017/0252571 A1* | 9/2017 | Dascoli ................ A61N 1/3925 |
| 2018/0028083 A1* | 2/2018 | Greenhut ............. A61N 1/3956 |
| 2018/0116537 A1 | 5/2018 | Sullivan et al. |

OTHER PUBLICATIONS

Heartstart MRx and XL AED Algorithm-Application Note, Jul. 2001, Edition 2 Philips Healthcare, USA.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Non-Final Office action dated Dec. 21, 2020, to U.S. Appl. No. 16/307,990.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

(56) References Cited

OTHER PUBLICATIONS

Examination Report No. 1 for Australian Patent Application No. 2018208710 dated Aug. 4, 2023.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

WITH "NO SHOCK" RECOMMENDATION

FIG. 5  *WITH INITIAL "SHOCK" RECOMMENDATION*

FIG. 6     *METHODS*

*SAMPLE ECG SEGMENT DEFINITION*

*H-F NOISE EVENT DETECTION IN ECG SEGMENTS PROXIMATE TO POTENTIAL R PEAKS*

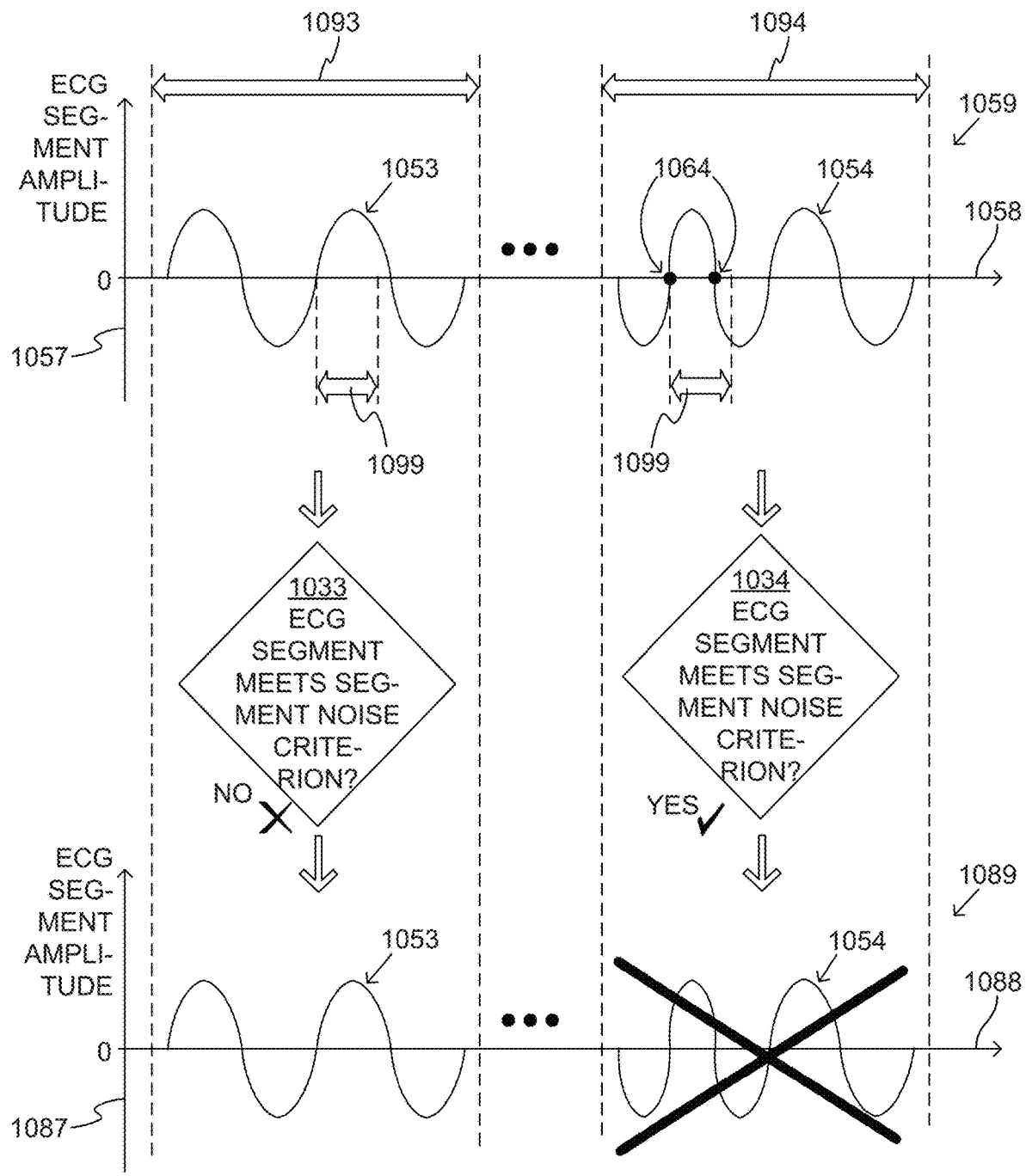
FIG. 10 — DETECTION OF H-F NOISE EVENT IN ECG SEGMENT BY SEGMENT NOISE CRITERION OF BRIEF PEAK(S)

WEARABLE CARDIOVERTER DEFIBRILLATOR (WCD) SYSTEM REACTING TO HIGH-FREQUENCY ECG NOISE

CROSS REFERENCE TO RELATED PATENT APPLICATIONS

The present application is a continuation of U.S. application Ser. No. 16/037,990 filed Jul. 17, 2018 (pending) which in turn claims the benefit of U.S. Provisional Patent Application No. 62/538,159, filed on Jul. 28, 2017. Said application Ser. No. 16/037,990 and said Application No. 62/538,159 are incorporated herein by reference in their entireties.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

Often the patient's ECG includes electrical noise, which can be created at the interface of the electrodes with the patient's skin. Such noise can make it difficult to diagnose the patient's condition accurately from the ECG, and detect whether or not the patient is having a shockable arrhythmia.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of wearable cardioverter defibrillator (WCD) systems, storage media that may store programs, and methods, the use of which may help overcome problems and limitations of the prior art.

In embodiments a WCD system is worn and/or carried by an ambulatory patient. The WCD system analyzes an ECG signal of the patient, to determine whether or not the patient should be given an electric shock to restart their heart. If the WCD system determines that such a shock should be given, then it also determines whether or not a High Frequency (H-F) noise criterion is met by the ECG signal. If that H-F noise criterion is not met, the patient can be shocked. If, however, that H-F noise criterion is met, then the WCD system can confirm before shocking, by sensing another portion of the ECG signal, analyzing again, and so on.

An advantage of embodiments is that, thanks to the confirmation before shocking, the possibility is diminished that the ECG signal will indicate that a shock is needed falsely, due to H-F noise. Furthermore, since the patient is alerted by an alarm before shocking, the incidence of false alarms can be diminished, and the patient may be more compliant in actually wearing and/or carrying the WCD system.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 10 shows sample time diagrams for illustrating other possible determinations about whether or not a segment noise criterion is met in individual ECG segments according to embodiments.

DETAILED DESCRIPTION

As has been mentioned, the present description is about wearable cardioverter defibrillator (WCD) systems, media that store instructions, and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
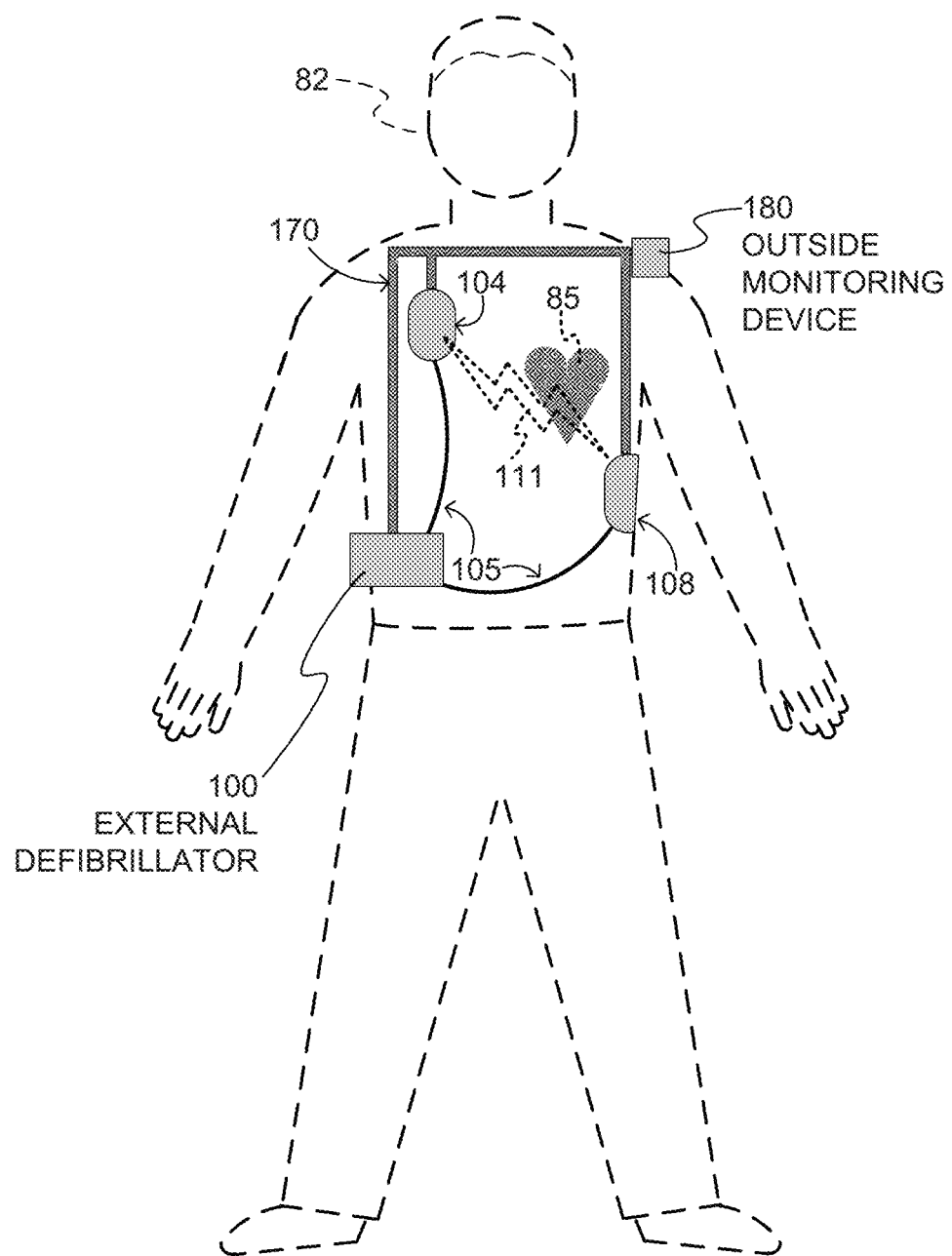
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
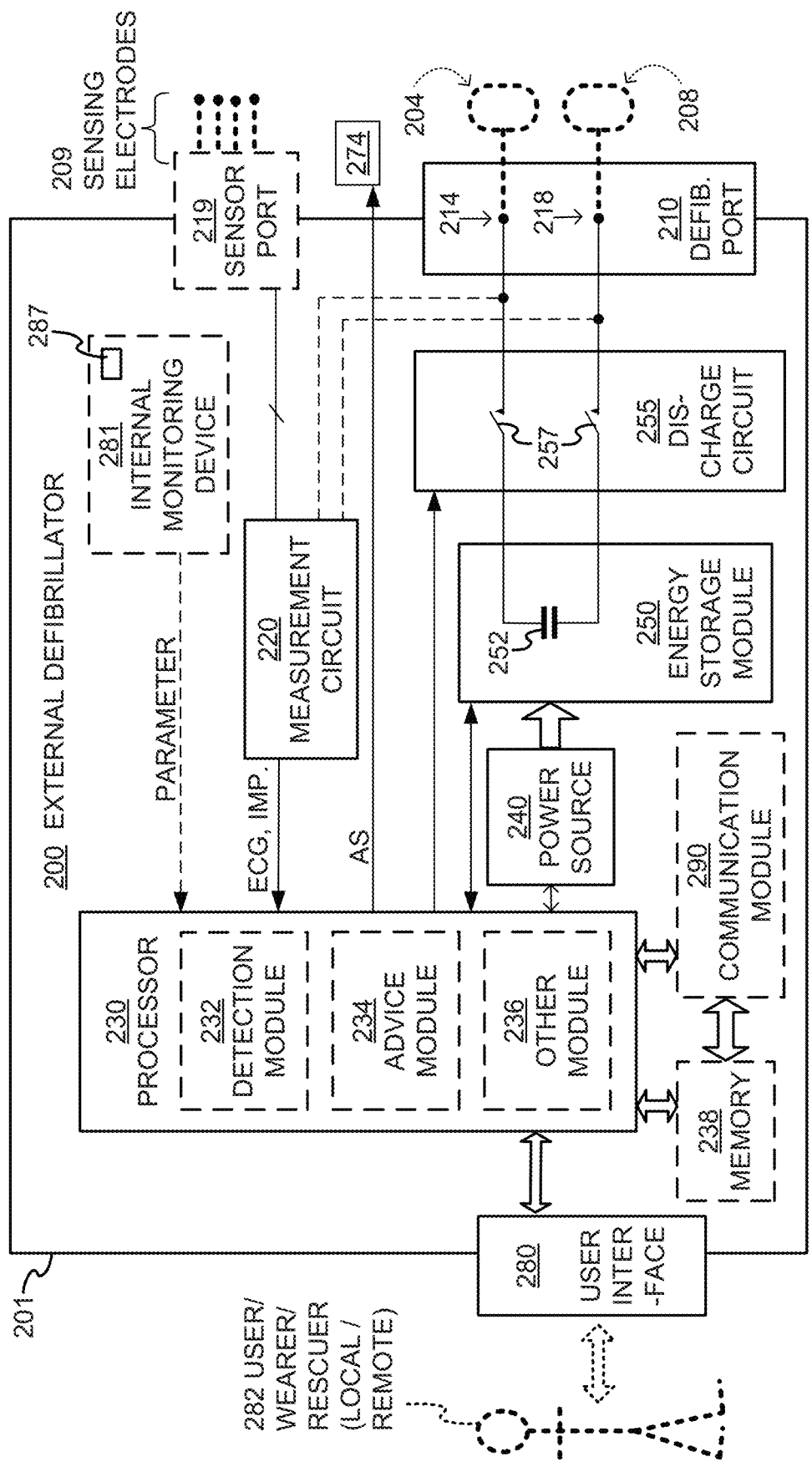
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

The intent for a WCD system is to shock when needed, and not shock when not needed. An ECG signal may provide sufficient data for making a shock/no shock determination. The problem is that, at any given point in time, some of these ECG signals may include noise, while others not. The noise may be due to patient movement, how well the electrodes contact the skin, and so on. The inventor has identified that some types of ECG noise for a WCD system can be classified as High-Frequency (H-F) noise, while other types of such ECG noise can be classified as High-Amplitude (H-A) noise. The noise problem for a WCD may be further exacerbated by the desire to use dry, non-adhesive monitoring electrodes. Dry, non-adhesive electrodes are thought to be more comfortable for the patient to wear in the long term, but may produce more noise than a conventional ECG monitoring electrode that includes adhesive to hold the electrode in place and an electrolyte gel to reduce the impedance of the electrode-skin interface.

Defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the physiological input reflects an ECG measurement. The patient parameter can be an ECG, which can be sensed as a voltage difference between electrodes 204, 208. In addition the patient parameter can be an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAA5), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Figure 3A:
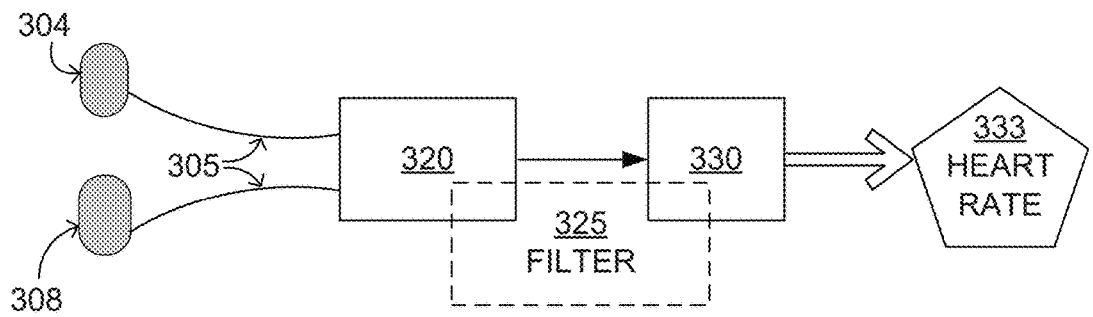
FIG. 3A is a diagram of selected components for illustrating how an ECG signal sensed by a pair of electrodes may be processed according to embodiments to yield a heart rate and other information.

Operations according to embodiments is now described in more detail. FIG. 3A is a conceptual diagram for illustrating how electrodes of a WCD system may sense or capture ECG signals of the patient, and how these sensed ECG signals may be used according to embodiments to yield a heart rate of the patient and other information. Two electrodes 304, 308 are attached to the torso of a patient, who is not shown. It will be appreciated that electrical noise may be introduced into the ECG signal at this point. Each of electrodes 304, 308 has a wire lead 305. Together, electrodes 304, 308 sense an ECG signal of the patient along a single vector. Additional ECG signals may be sensed along additional vectors.

FIG. 3A also shows a measurement circuit 320 and a processor 330, which can be made as described for measurement circuit 220 and processor 230. A filter 325 is optionally implemented in measurement circuit 320 and/or in processor 330. Filter 325 may be implemented as an analog filter, a digital filter, and so on. Filter 325 may help overcome some types of ECG noise by suppressing it, making this noise easier to detect, and so on. Processor 330 may further compute a heart rate 333 according to embodiments, as described in more detail further in this document. Computed heart rate 333 may be stored in memory 238. Heart rate 333 may then be downloaded later from memory 238, transmitted wirelessly via communication module 290, displayed by a screen of user interface 280, and so on.

Figure 3B:
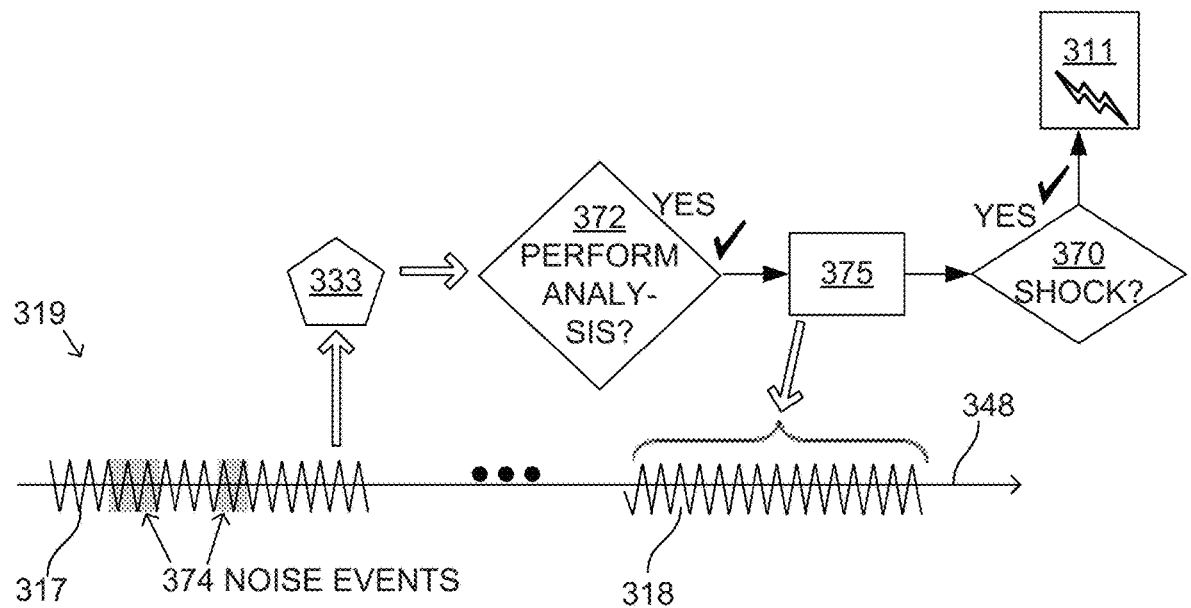
FIG. 3B is a conceptual diagram for illustrating examples of how a first ECG signal may be used for a heart rate computation even if it includes noise events, while a second ECG signal may be used for performing an analysis and/or confirming a shock decision according to embodiments.

FIG. 3B is a conceptual diagram that includes a time axis 348. A sample ECG signal 319 of a patient is shown with reference to time axis 348. ECG signal 319 is intended to be drawn generically, and could appear having a waveform different from what is shown in FIG. 3B. It will be recognized that, in the instances where an ECG signal actually has the exact appearance seen in FIG. 3B, that ECG signal might indicate VT, or even VF, but that is only for example.

ECG signal 319 has a first portion 317 and a second portion 318. Second portion 318 has been sensed after sensing first portion 317. Such ECG signal portions can be defined in a number of ways. For example, ECG portions 317, 318 can be a part of the sensed ECG signal that processor 230 processes at one time. An ECG portion may be long enough to perform a full ECG rhythm analysis. As such, An ECG portion may include several QRS complexes.

Or an ECG portion may be shorter. In addition, first portion 317 includes noise events 374, examples of which are described in more detail elsewhere in this document. And, while noise events 374 are shown in FIG. 3B as definite events, occurring at specific times and having specific durations, etc., that is done only for purposes of discussion. In real life, noise events in the ECG signal do not announce themselves. Rather, embodiments of this disclosure detect when certain types of noise are within an ECG signal, react accordingly, and so on.

First ECG signal portion 317 may result in computing heart rate 333 according to embodiments. Then a decision diamond 372 indicates that a decision may be made as to whether or not an analysis should be performed. The analysis can be a full ECG analysis, or a confirmation of the heart rate computation, and so on. The answer for decision diamond 372 may be provided by the value of heart rate 333, which was derived from first signal portion 317. For example, a certain range of values for heart rate 333 may give a NO answer, which is not indicated in FIG. 3B. However, another range of values for heart rate 333 may give a YES answer, which is also indicated in FIG. 3B with a check mark. If the answer is YES, then according to an analysis operation 375, second ECG signal portion 318 may be analyzed. As part of this analysis, second ECG portion 318 may be used to determine whether or not a shock criterion is met, for example by advice module 234.

According to another decision diamond 370, another decision is indicated as to whether or not a shock should be delivered. The answer for decision diamond 370 may be provided by the result of analysis operation 375. A NO answer is not indicated in FIG. 3B. Else, if the answer is YES, then according to a shock operation 311, a shock 111 is administered to patient 82. For shock operation 311, processor 230 may control, responsive to a shock criterion being met, discharge circuit 255 to discharge through patient 82 an electrical charge that is stored in energy storage module 250, while support structure 170 is worn by patient 82 so as to deliver a shock 111 to patient 82. Of course, before shock operation 311 another process may be undertaken where the patient is alerted by an alarm, challenged to demonstrate they are alive, and so on.

Operations 370 and 375 may be performed in a number of ways. For instance, the heart rate 333 may be computed again, for confirmation of the value arrived at in the first time. It may be computed in the same way, or a different way, for example with additional safeguards, such as for addressing noise. Plus, more parameters may be computed, such as a QRS width and so on.

Operations are now described where a WCD system reacts to high frequency ECG noise according to embodiments. These operations can be broadly divided in situations where the ECG signal a) does not meet a shock criterion, some of which are described in FIG. 4, and b) meets a shock criterion, some of which are described in FIG. 5. These operations may refer to segments of the ECG signal including or not including high frequency (H-F) noise events. The determination of whether such H-F noise events are included or not may be made depending on whether or not a High-Frequency (H-F) noise criterion is met, a segment noise criterion is met, and so on, more of which is described in more detail later in this document.

Figure 4:
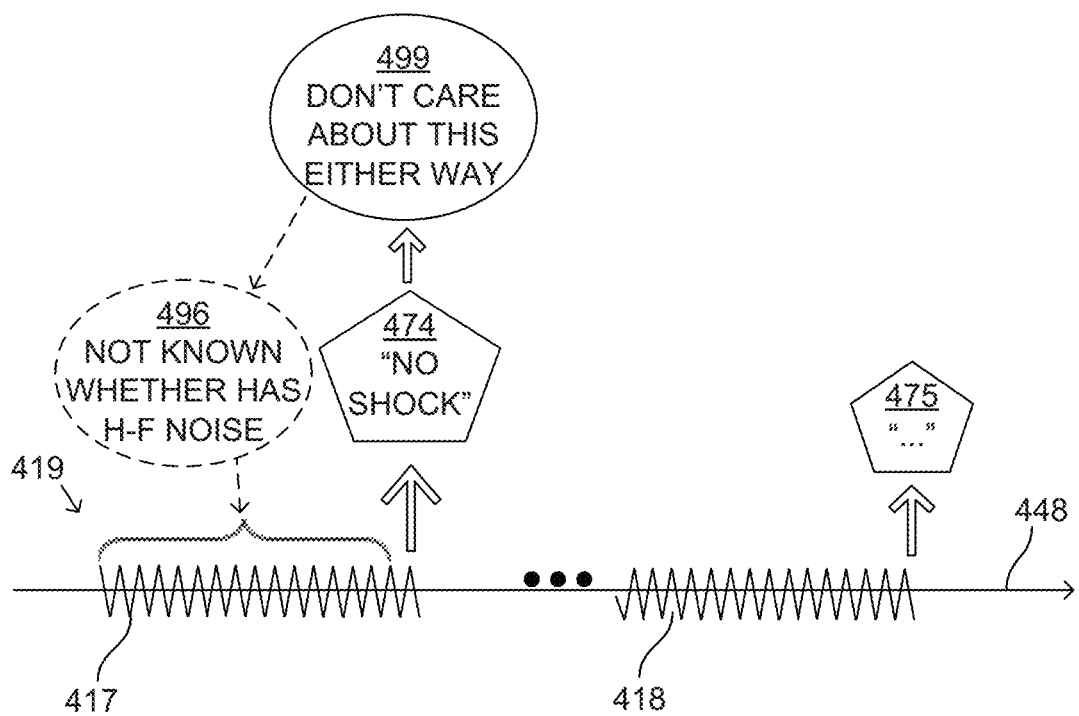
FIG. 4 is a conceptual diagram for illustrating sample possible determinations made about the patient from portions of the patient's ECG signal according to embodiments.

FIG. 4 is a conceptual diagram that includes a time axis 448. A sample ECG signal 419 of a patient is shown with reference to time axis 448. ECG signal 419 is intended to be drawn generically, similarly with ECG signal 319 of FIG. 3B. ECG signal 419 has a first portion 417 and a second portion 418. Second portion 418 has been sensed after sensing first portion 417. A comment oval 496 contains the comment that it is not known, at this time, whether or not first ECG portion 417 includes H-F noise.

In the example of FIG. 4, an analysis is made from first ECG signal portion 417. This analysis may be performed, for example, as described for decision diamond 370. From that analysis, it has been determined that a first shock criterion is not met. In other words, first ECG signal portion 417 did not merit the WCD system administering a shock to the patient. In FIG. 4, this determination is shown by a determination pentagon 474, which includes the words "NO SHOCK".

It should be noted that determination pentagon 474 was arrived at subject to comment oval 496. However, since determination pentagon 474 is "NO SHOCK" then, according to another comment oval 499, the WCD system does not care about comment oval 496. In other words, in this instance determination pentagon 474 stands as the WCD system's determination, regardless of whether or not H-F noise events are included in ECG segments of first ECG portion 417. As such, since determination pentagon 474 was "NO SHOCK", any H-F noise in first ECG portion 417 is ignored.

The process may then continue with the second ECG portion 418, which is subsequent to first ECG portion 417, because it is sensed subsequently to it. Another determination pentagon 475 may be arrived at, and so on.

Figure 5:
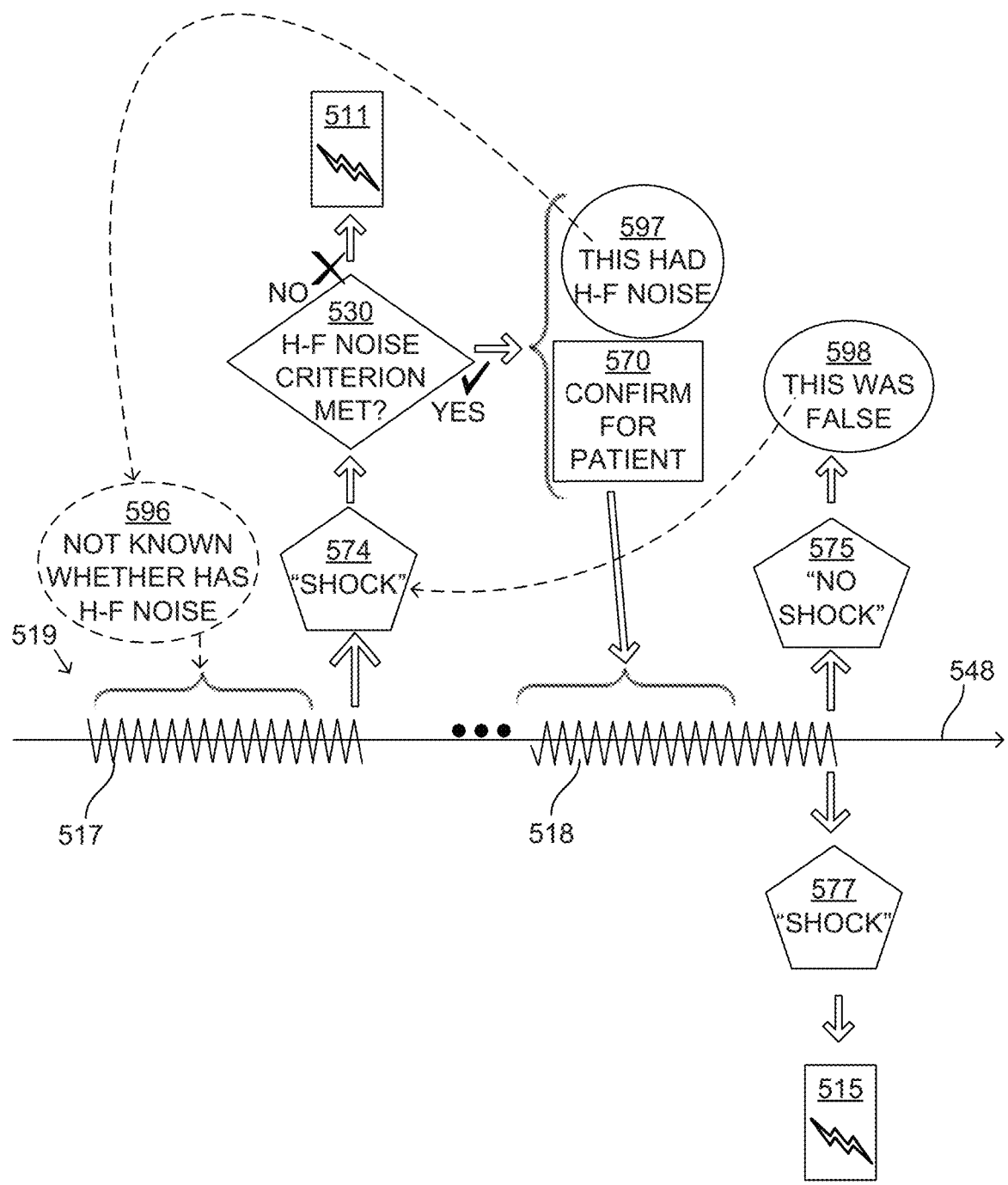
FIG. 5 is a conceptual diagram for illustrating other sample possible determinations made about the patient from portions of the patient's ECG signal according to additional embodiments.

FIG. 5 is a conceptual diagram that includes a time axis 548. A sample ECG signal 519 of a patient is shown with reference to time axis 548. ECG signal 519 is intended to be drawn generically, similarly with ECG signal 419 of FIG. 4. ECG signal 519 has a first portion 517 and a second portion 518. Second portion 518 has been sensed after sensing first portion 517. A comment oval 596 contains the comment that it is not known, at this time, whether or not first ECG portion 517 includes H-F noise.

In the example of FIG. 5, an analysis is made from first ECG signal portion 517. This analysis may be performed, for example, as described for decision diamond 370. From that analysis, it has been determined that a first shock criterion is indeed met. In other words, first ECG signal portion 517 merits the WCD system administering a shock to the patient. In FIG. 5, this determination is shown by a determination pentagon 574, which includes the word "SHOCK". In this situation, however, the possibility of H-F noise will not be ignored as it was ignored in FIG. 4.

Indeed, according to another decision diamond 530, it is determined whether or not first ECG portion 517 meets a High-Frequency (H-F) noise criterion. Sample such criteria are described later in this document. In this example, the possible answers to decision diamond 530 are NO, denoted by an "X" and YES, denoted by a checkmark. If the answer is NO then, according to an operation 511 a shock is administered to the patient, similarly with operation 311.

If the answer to decision diamond 530 is yes, then a comment oval 597 indicates that comment oval 596 is determined to have been H-F noise. According to a related operation 570, it can be determined from second portion 518 of the sensed ECG signal, whether or not a shock criterion is met. This operation 570 may be performed, for example, as described for decision diamond 370. The determination that is arrived at this way is either determination pentagon 575 ("NO SHOCK"), or determination pentagon 577 ("SHOCK"). Determination pentagon 575 ("NO SHOCK") is associated with comment oval 598, which indicates that determination pentagon 574 ("SHOCK") was false, and probably arrived at due to H-F noise. On the other hand, determination pentagon 577 ("SHOCK") can be followed by an operation 515 similar to operation 511, where a shock is administered to the patient, and so on.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 6:
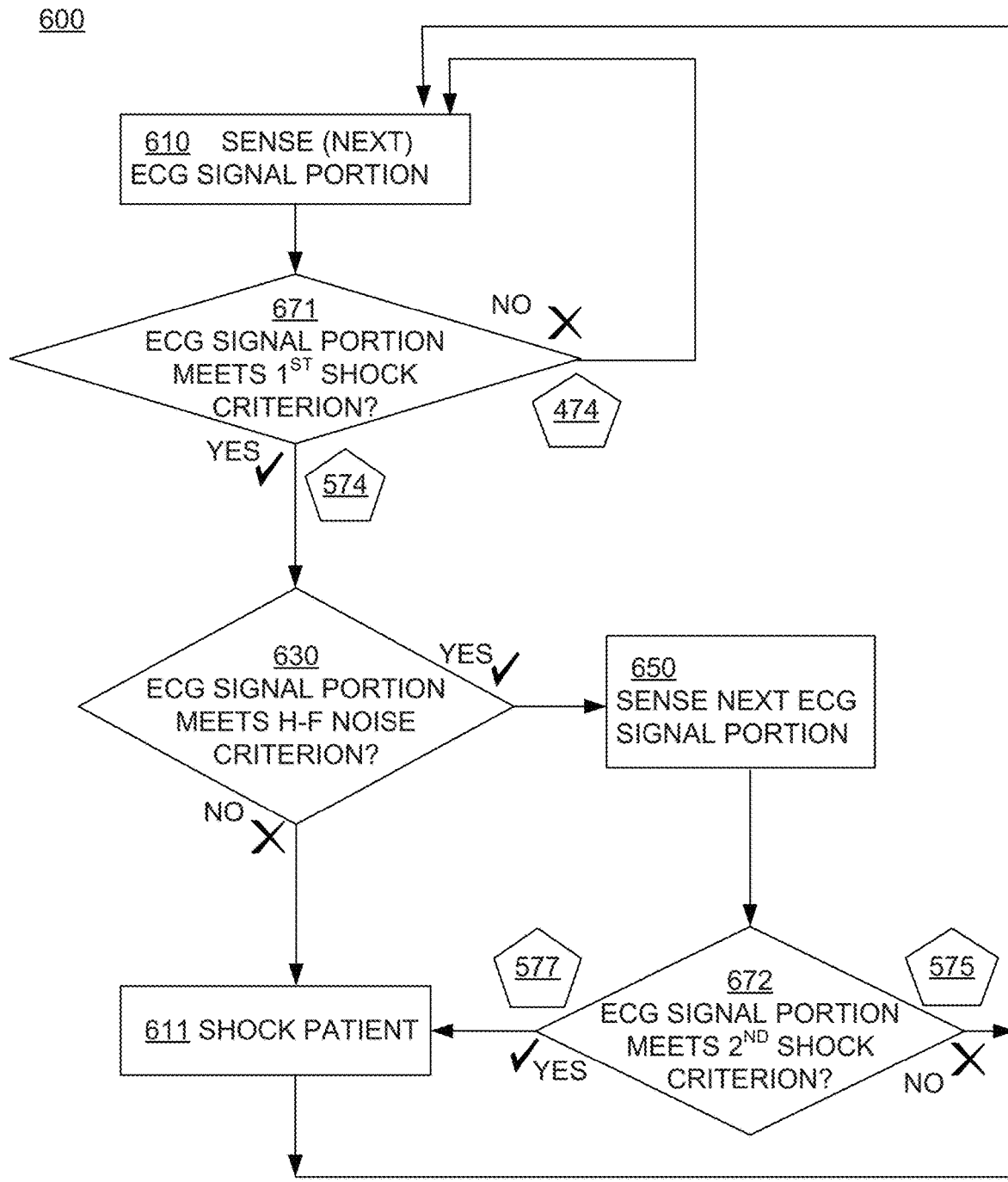
FIG. 6 is a flowchart for illustrating sample methods according to embodiments.

FIG. 6 shows a flowchart 600 for describing methods according to embodiments. Flowchart 600 includes operations that are linked by arrows. In addition, flowchart 600 is annotated with determination pentagons repeated from FIG. 4 and FIG. 5 where applicable.

According to an operation 610, a portion is sensed of an ECG signal of the patient. Such portions can be sensed sequentially, for example as seen above with ECG signal portions pairs 317 & 318, 417 & 418 and 517 & 518.

A subsequent operation 671 is also a decision diamond 671. According to operation 671, it can be determined whether or not a first shock criterion is met. The determination can be made from the signal portion sensed at operation 610. The shock criterion can be the same as that of decision diamond 370, or different. If, at decision diamond 671 the answer is NO, then that is equivalent to determination pentagon 474 of FIG. 4, and execution may return to another operation, such as operation 610.

If, at decision diamond 671 the answer is YES, then that is equivalent to determination pentagon 574 of FIG. 5. Then execution may proceed to another operation 630, which is also a decision diamond 630. According to operation 630, it can be determined whether or not the first portion of the sensed ECG signal, which met the first shock criterion of operation 671, also meets a High-Frequency (H-F) noise criterion. Examples of such noise criteria are described later in this document.

If, at decision diamond 630 the answer is NO, then execution may proceed to another operation 611 and shock the patient, similarly with operation 511. After that, execution may return to another operation, such as operation 610.

If, at decision diamond 630 the answer is YES, then execution may proceed to another operation 650 where a next, or second, portion of the ECG signal can be sensed. In other words, operation 650 is similar to operation 610.

Execution may then proceed to operation 672, which is also a decision diamond 672. According to operation 672, it may be determined, from the second portion of the sensed ECG signal, whether or not a second shock criterion is met. The second shock criterion can be the same or different as the first shock criterion. This second portion of the ECG signal can be sensed and analyzed for purposes of confirmation of the YES answer at decision diamond 671.

If, at decision diamond 672 the answer is NO, then that is equivalent to determination pentagon 575 of FIG. 4, and execution may return to another operation, such as operation 610.

If, at decision diamond 672 the answer is YES, then that is equivalent to determination pentagon 577 of FIG. 5. Then execution may proceed to operation 611, and the patient is shocked, as above. It will be understood, however, that the path to operation 611 via a YES answer at decision diamond 630, and then operations 650 and 672 may take longer than the path through a NO answer at decision diamond 630. As such, the shock of operation 611 maybe delivered at least 5 seconds later than the shock that would have been delivered responsive to the H-F noise criterion not being met at operation 630.

Noise criteria according to embodiments are now described in more detail. In some embodiments, a potential R peak of a QRS complex is identified in a first portion of the sensed ECG signal. Then an ECG segment becomes defined as a segment of the ECG signal that corresponds to the potential R peak. It is preferred that the ECG segment becomes defined in proximity with the potential R peak, and in fact maybe even include the potential R peak that it corresponds to. Then the H-F noise criterion can be met responsive to the ECG segment meeting a segment noise criterion. Examples are now described.

Figure 7:
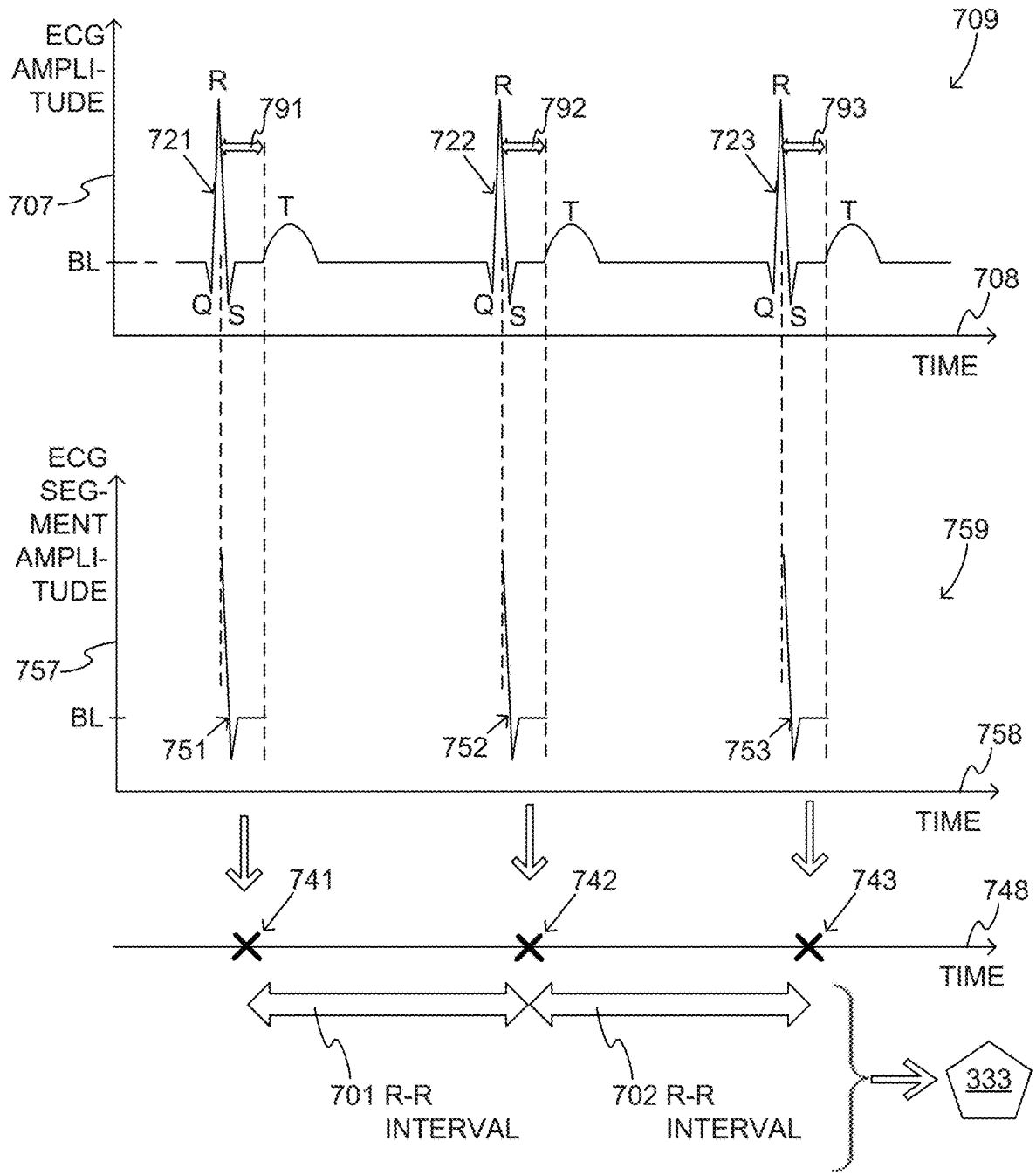
FIG. 7 shows sample time diagrams for illustrating an example of how a patient's ECG signal may be segmented and for how a patient's heart rate may be computed according to embodiments.

FIG. 7 shows an ECG signal of patient 82 in a time diagram 709. Diagram 709 has an ECG amplitude axis 707 and a time axis 708. The shown ECG signal is somewhat-idealized, noise-free, and includes three full heartbeats. In particular, the ECG signal includes three QRS complexes, each of which is followed by a T-wave of lesser amplitude. These QRS complexes include three R peaks 721, 722, 723. The ECG signal hovers around a horizontal baseline value BL. Baseline value BL can be considered to be zero, but in real life it might be changing value, possibly due to noise. In this somewhat-idealized ECG signal, a P-wave before the QRS complex and a U-wave after the QRS complex are not shown at all.

Even though the ECG signal of diagram 709 is somewhat-idealized, it serves as a good basis for describing embodiments, as if it were the ECG signal that was sensed. For example, R peaks 721, 722, 723 can be detected in an ECG signal of patient 82, even if that signal contains noise. These R peaks 721, 722, 723 can be used for detecting the patient's heart rate 333, because their large amplitude relative to the remainder of the ECG signal makes them more easy to identify and/or detect. In particular, in diagram 709, three ECG segments are defined according to embodiments, as segments of ECG signal portion that include R peaks 721, 722, 723 respectively.

FIG. 7 shows ECG segments more explicitly in another time diagram 759. Diagram 759 has an ECG Segment Amplitude axis 757 and a time axis 758. ECG segments 751, 752, 753 are segments of the ECG signal of diagram 709 that are within respective time windows 791, 792, 793. As such, ECG segments 751, 752, 753 have the same duration as the duration of time windows 791, 792, 793.

An ECG segment according to embodiments can be defined to have a duration that isolates the potential R peak from other features. For example, an ECG segment can have a duration between 160 ms and 200 ms, such as 180 milliseconds. In FIG. 7, that duration is shown as the width of time windows 791, 792, 793.

An ECG segment according to embodiments can be defined to correspond to an R peak of an ECG signal as a segment of the ECG signal that includes the R peak. In some embodiments, the ECG segment starts at the potential R peak, as in the example of FIG. 7. In other embodiments, the ECG segment starts before the potential R peak and ends after it. For example, the potential R peak can be at the center of the ECG segment. As seen later in this document, a segment can be used to analyze the validity of a potential R peak.

It will be understood that R peaks 721, 722, 723 can be identified as potential R peaks, if the ECG signal of diagram 709 is the sensed ECG signal. In that case the ECG segments 751, 752, 753 can be defined to include potential R peaks 721, 722, 723.

FIG. 7 also shows a time axis 748 that indicates only the time occurrences 741, 742, 743 of R peaks 721, 722, 723, respectively. Moreover, these R peaks 721, 722, 723 can be considered in pairs of successive R peaks, to define time intervals. In particular, the pair of peaks 721 and 722 defines a time interval 701 from time occurrences 741, 742, while the pair of peaks 722 and 723 defines a time interval 702 from time occurrences 742, 743. Time intervals 701, 702 are sometimes called R-R intervals of the ECG signal. The durations of time intervals 701, 702 can be measured, and heart rate 333 of the patient can be thus computed from them.

It will be recognized that this process of computing heart rate 333 from peaks 721, 722, 723 in the ECG signal is the same regardless of how these peaks 721, 722, 723 are detected. Medical devices sometimes measure the ECG signal electronically and focus on these peaks to detect the R-R interval, for example as per the above. Other times, peaks 721, 722, 723 correspond with peaks in the patient's blood pressure, which can be sensed by a person placing their hand against the neck or a wrist of a patient.

It can be more difficult, however, to measure the patient's heart rate from these peaks in the presence of noise in the ECG signal. An example is are now described.

Figure 8:
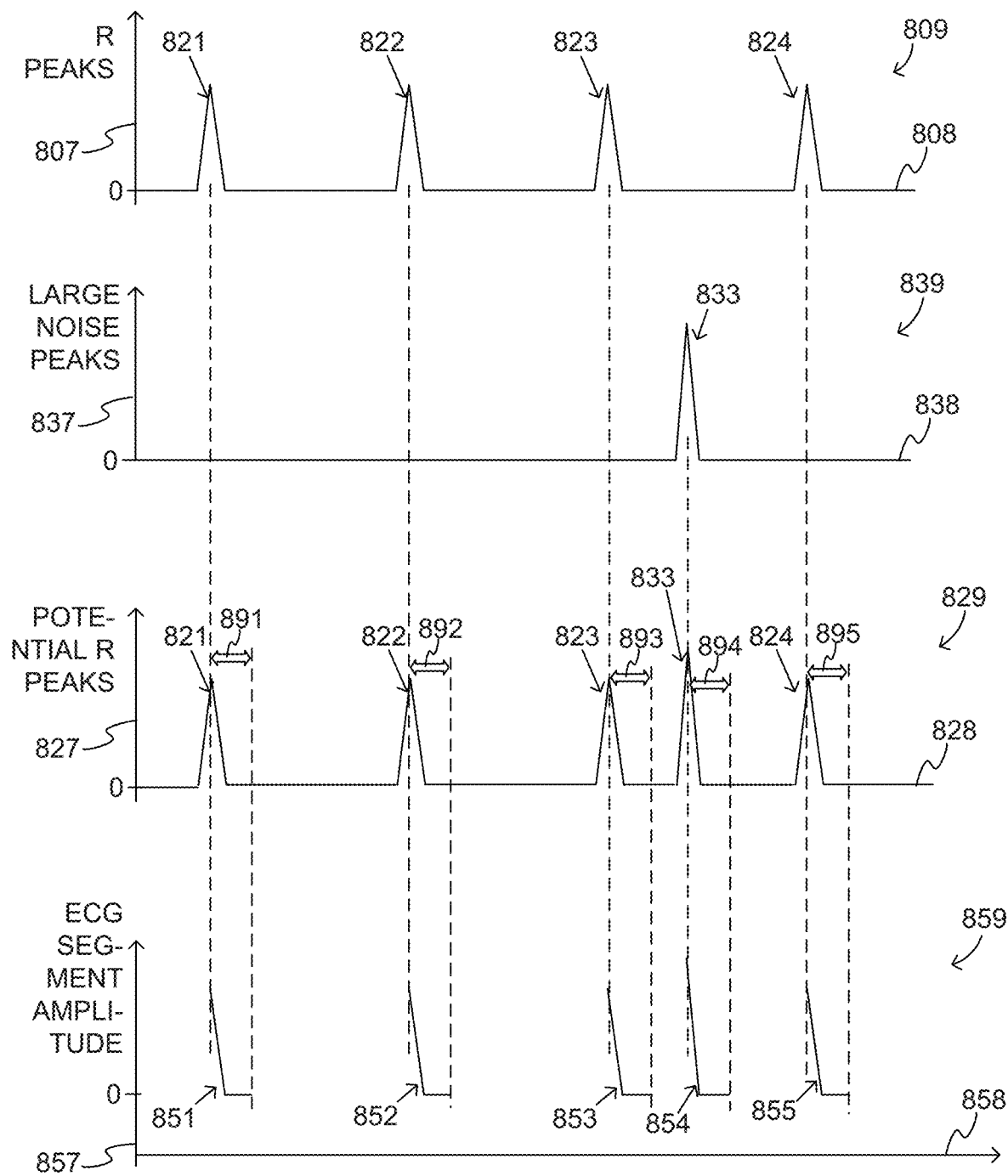
FIG. 8 shows sample time diagrams for illustrating how a patient's detected ECG signal may be segmented for detecting noise events according to embodiments.

FIG. 8 shows a time diagram 809. Diagram 809 has an R peaks axis 807 and a time axis 808. Diagram 809 depicts only R peaks 821, 822, 823, 824 of a patient's ECG signal portion, with all other values of the ECG signal being shown as zero for simplification. This simplification is acceptable in this instance, as FIG. 8 is used for discussing ECG segments as per the above, where large peaks are being detected.

FIG. 8 also shows a time diagram 839 to depict sample noise that could be added to the ECG of diagram 829. Diagram 839 has a Large Noise Peaks axis 837 and a time axis 838. Diagram 839 depicts only one large noise peak 833, with all other values being shown as zero for simplification, since large peaks are being detected. It will be recognized that noise peak 833 is an example of a noise event 374.

FIG. 8 also shows a time diagram 829. Diagram 829 has a Potential R Peaks axis 827 and a time axis 828. Time diagram 829 depicts the suspected or potential R peaks of a sample sensed ECG signal portion. Time diagram 829 in this example is arrived at as a sum of time diagrams 809 and 839.

According to embodiments, therefore, there are five potential R peaks 821, 822, 823, 833, 824 in time diagram 829. Given the arrangement of the drawings above, the reader can tell that, of these potential R peaks 821, 822, 823, 833, 824, one of them (833) is false due to noise, while the other ones are true. As such, large noise peak 833 represents a false detection of a QRS complex. This threatens the accuracy of the calculation of heart rate 333, as will be understood from the intercepts in time axis 748 of FIG. 7; indeed, more such time intercepts may falsely indicate that the patient is having tachycardia or worse.

In embodiments, this risk is addressed by defining ECG segments 851, 852, 853, 854, 855 as segments of ECG signal portion in time diagram 809 that include the identified potential R peaks 821, 822, 823, 833, 824 respectively. Such may be implemented by first defining time windows 891, 892, 893, 894, 895 starting from these identified potential R peaks 821, 822, 823, 833, 824.

FIG. 8 shows ECG segments 851, 852, 853, 854, 855 more explicitly in another time diagram 859. Diagram 859 has an ECG Segment Amplitude axis 857 and a time axis 858. ECG segments 851, 852, 853, 854, 855 are segments of the ECG signal of diagram 829 that are within respective time windows 891, 892, 893, 894, 895. As such, ECG segments 851, 852, 853, 854, 855 have the same duration as the duration of time windows 891, 892, 893, 894, 895.

In embodiments, ECG segments 851, 852, 853, 854, 855 can be used to detect which of these potential R peaks is noise. In some embodiments, the H-F noise criterion may be met responsive to the ECG segment meeting a segment noise criterion.

In the sample embodiments that are described below, the ECG signal portion and/or the ECG segment may be first filtered, for example by filter 325. For instance, filter 325 may be a filter passing frequencies between 8 Hz and 25 Hz. In such embodiments, the H-F noise criterion is met responsive to the filtered ECG segment meeting the segment noise criterion.

Two examples of segment noise criteria are now described.

Figure 9:
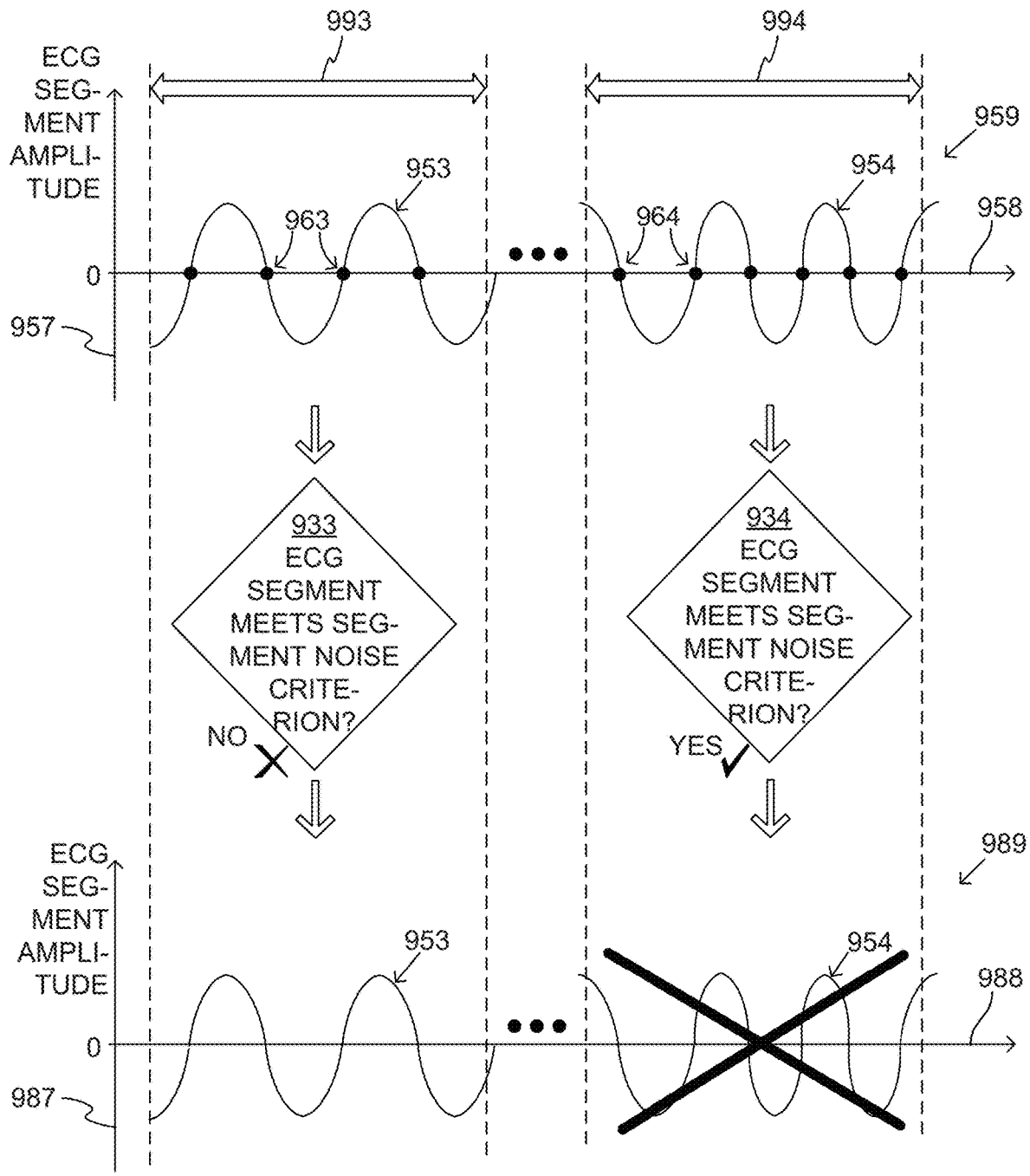
FIG. 9 shows sample time diagrams for illustrating possible determinations about whether or not a segment noise criterion is met in individual ECG segments according to embodiments.

FIG. 9 shows a time diagram 959. Diagram 959 has an ECG segment amplitude axis 957 and a time axis 958. Diagram 959 depicts two sample ECG segments 953, 954, which have been defined by respective time windows 993, 994. In turn, time windows 993, 994 correspond to potential R peaks of a sensed ECG signal portion, and maybe even include these R peaks.

In FIG. 9, ECG segments 953, 954 are shown as approximately sinusoidal waveforms, but that is only by way of example. For instance, these waveforms are rounded where they have local maxima and local minima, but they could have edges there instead of being rounded, such as ECG signal 319. In fact, in embodiments where the ECG segment includes a suspected or potential R peak of a QRS complex, one of the edges is sharp and its pulse can have much higher amplitude than its neighboring pulses. These waveforms being rounded, however, is adequate for this particular explanation.

According to decision diamonds 933, 934, ECG segments 953, 954 are subjected to determinations of whether or not a segment noise criterion is met. In some embodiments, the criteria of decision diamonds 933, 934 are the same, while in others different. In some embodiments, an ECG segment is subjected to more than one segment noise criterion, and so on.

In this example, the segment noise criterion is met responsive to the ECG segment containing more zero-crossings than a crossings threshold. The crossings threshold can be advantageously determined by the chosen duration of time windows 993, 994, and given a target density or frequency of zero crossings.

In this example the crossings threshold is five. ECG segment 953 has four zero crossings 963, which are not more than the threshold of five. As such, the segment noise criterion is not met, and the answer to decision diamond 933 is NO. On the other hand, ECG segment 954 has six zero crossings 964, which are more than the threshold of five. As such, the segment noise criterion is met, and the answer to decision diamond 934 is YES.

FIG. 9 also shows a time diagram 989. Diagram 989 has an ECG segment amplitude axis 987 and a time axis 988. Diagram 989 depicts the ECG segments of diagram 959 that survive the segment noise criterion of decision diamonds 933, 934. As such, ECG segment 953 survives, while ECG segment 954 is discarded. Accordingly, the R peak that gave rise to segment 954 can be discarded as being due to H-F noise, and a more accurate result can be reached by the algorithm of the WCD system.

FIG. 10 shows a time diagram 1059. Diagram 1059 has an ECG segment amplitude axis 1057 and a time axis 1058. Diagram 1059 depicts two sample ECG segments 1053, 1054, which have been defined by respective time windows 1093, 1094 that are near potential R peaks of an ECG signal portion. In turn, time windows 1093, 1094 correspond to potential R peaks of a sensed ECG signal portion, and maybe even include these R peaks.

In FIG. 10, ECG segments 1053, 1054 are shown as approximately sinusoidal waveforms, but that is only by way of example. For instance, these waveforms could have edges instead of being rounded at their local maxima and local minima. In fact, in embodiments where the ECG segment includes a suspected or potential R peak of a QRS complex, one of the edges is sharp and its pulse can have much higher amplitude than its neighboring pulses. These waveforms being rounded is adequate for this particular explanation.

According to decision diamonds 1033, 1034, ECG segments 1053, 1054 are subjected to determinations of whether or not a segment noise criterion is met. In this example, the segment noise criterion is met responsive to the ECG segment containing at least one peak briefer than a threshold duration. In some embodiments, the threshold duration is 25 milliseconds (ms).

In this example the threshold duration is shown as a time window 1099. ECG segment 1053 has no pulse more brief or shorter than time window 1099. As such, the segment noise criterion is not met, and the answer to decision diamond 1033 is NO. On the other hand, ECG segment 1054 has at least one pulse more brief than time window 1099, for instance as evidenced by zero crossing 1064. As such, the segment noise criterion is met, and the answer to decision diamond 1034 is YES.

FIG. 10 also shows a time diagram 1089. Diagram 1089 has an ECG segment amplitude axis 1087 and a time axis 1088. Diagram 1089 depicts the ECG segments of diagram 1059 that survive the segment noise criterion of decision diamonds 1033, 1034. As such, ECG segment 1053 survives, while ECG segment 1054 is discarded. Accordingly, the R peak that gave rise to segment 1054 can be discarded as being due to H-F noise, and a more accurate result can be reached by the algorithm of the WCD system.

In other embodiments a noisiness ratio can be used for ECG portion 517. The noisiness ratio can be defined from a number of segments within portion 517 that meet the segment noise criterion over the total number of potential R peaks within portion 517. In such embodiments, the H-F noise criterion can be met instead responsive to the noisiness ratio exceeding a threshold.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method for a wearable cardioverter defibrillator (WCD) system, the WCD system including a support structure worn by an ambulatory patient, an energy storage module storing an electrical charge, a discharge circuit coupled to the energy storage module, electrodes, and a processor, the method comprising:
   sensing, via the electrodes, an Electrocardiogram (ECG) signal of the patient;
   determining, from a first portion of the sensed ECG signal, whether a first shock criterion is met;
   determining whether the first portion of the sensed ECG signal meets a High-Frequency (H-F) noise criterion, wherein the H-F noise criterion being met comprises the sensed ECG signal containing a peak with a duration of 25 milliseconds (ms) or less;
   identifying a potential R peak of a QRS complex in the first portion of the sensed ECG signal;
   defining an ECG segment as a segment of the first portion of the ECG signal that corresponds to the potential R peak;
   determining whether the H-F noise criterion is met responsive to the ECG segment meeting a segment noise criterion, the segment noise criterion being met responsive to the ECG segment containing at least one peak briefer than a threshold duration of 25 ms; and
   responsive to the first shock criterion being met and the H-F noise criterion not being met, discharging, via the discharge circuit, the stored electrical charge through the patient while the support structure is worn by the patient to deliver a shock to the patient, else
   responsive to the first shock criterion being met and the H-F noise criterion being met, determining, from a second portion of the sensed ECG signal, whether a second shock criterion is met, the second portion sensed subsequently to the first portion, and
   responsive to the second shock criterion being met, discharging, via the discharge circuit, the stored electrical charge through the patient while the support structure is worn by the patient to deliver a shock to the patient.

2. The method of claim 1, wherein
the second shock criterion is the same as the first shock criterion.

3. The method of claim 1, wherein
a potential R peak of a QRS complex is identified in the first portion of the sensed ECG signal,
an ECG segment becomes defined as a segment of the first portion of the ECG signal that corresponds to the potential R peak, and
the H-F noise criterion is met responsive to the ECG segment meeting a segment noise criterion.

4. The method of claim 3, wherein
the ECG segment includes the potential R peak that it corresponds to.

5. The method of claim 3, wherein
the ECG segment starts at the potential R peak that it corresponds to.

6. The method of claim 3, wherein
the ECG segment has a duration between 160 ms and 200 ms.

7. The method of claim 3, wherein
the ECG segment is filtered, and
the H-F noise criterion is met responsive to the filtered ECG segment meeting the segment noise criterion.

8. The method of claim 7, wherein
the ECG segment is thus filtered with a filter passing frequencies between 8 Hz and 25 Hz.

9. The method of claim 7, wherein
the ECG segment has a duration between 160 ms and 200 ms.

10. The method of claim 7, wherein
the ECG segment starts at the potential R peak that it corresponds to.

11. The method of claim 3, wherein
the segment noise criterion is met responsive to the ECG segment containing more zero-crossings than a crossings threshold.

12. The method of claim 11, wherein
the crossings threshold is five.

13. The method of claim 11, wherein
the ECG segment has a duration between 160 ms and 200 ms.

14. The method of claim 3, wherein the segment noise criterion is met responsive to the ECG segment containing at least one peak briefer than a threshold duration.

15. The method of claim 14, wherein the threshold duration is 25 ms.

16. The method of claim 14, wherein the ECG segment has a duration between 160 ms and 200 ms.

* * * * *